(12) United States Patent
Bien et al.

(10) Patent No.: US 11,317,836 B2
(45) Date of Patent: May 3, 2022

(54) IMPLANTABLE BLOOD GLUCOSE MEASURING APPARATUS AND METHOD

(71) Applicant: UNIST (ULSAN NATIONAL INSTITUTE OF SCIENCE AND TECHNOLOGY), Uljugun Ulsan (KR)

(72) Inventors: Franklin Don Bien, Ulju-gun Ulsan (KR); Hee Don Jang, Ulju-guh Ulsan (KR); Kyung Min Na, Ulju-gun Ulsan (KR)

(73) Assignee: UNIST (ULSAN NATIONAL INSTITUTE OF SCIENCE AND TECHNOLOGY), Ulju-gun Ulsan (KR)

( * ) Notice: Subject to any disclaimer, the term of this patent is extended or adjusted under 35 U.S.C. 154(b) by 267 days.

(21) Appl. No.: 16/347,897

(22) PCT Filed: Sep. 20, 2017

(86) PCT No.: PCT/KR2017/010302
§ 371 (c)(1),
(2) Date: May 7, 2019

(87) PCT Pub. No.: WO2018/139727
PCT Pub. Date: Aug. 2, 2018

(65) Prior Publication Data
US 2019/0254576 A1  Aug. 22, 2019

(30) Foreign Application Priority Data

Jan. 26, 2017 (KR) ........................ 10-2017-0012877

(51) Int. Cl.
*A61B 5/145* (2006.01)
*A61B 5/0507* (2021.01)
(Continued)

(52) U.S. Cl.
CPC ........ *A61B 5/14532* (2013.01); *A61B 5/0004* (2013.01); *A61B 5/0031* (2013.01);
(Continued)

(58) Field of Classification Search
CPC .............. A61B 5/14532; A61B 5/0031; A61B 2562/166; A61B 5/0004; A61B 5/1473;
(Continued)

(56) References Cited

U.S. PATENT DOCUMENTS

2003/0033102 A1* 2/2003 Dietiker ............... A61B 5/1495
702/85
2012/0136278 A1* 5/2012 Gupta .................... A61B 5/076
600/595

(Continued)

FOREIGN PATENT DOCUMENTS

JP 2005-192821 A 7/2005
JP 2008-505715 A 2/2008
(Continued)

OTHER PUBLICATIONS

Sidley, M. (Jun. 10, 2013). "Calibration for real-time non-invasive blood glucose monitoring" Order No. 1540160. Rochester Institute of Technology, 2013. Ann Arbor: ProQuest. (Year: 2013).*
(Continued)

*Primary Examiner* — Etsub D Berhanu
(74) *Attorney, Agent, or Firm* — von Briesen & Rope, s.c.

(57) ABSTRACT

The present invention relates to non-invasive blood glucose measuring apparatus and method. More specifically, the apparatus is inserted into a blood vessel of a human body, and at a point of time when a measurement is desired, wirelessly transmits power so as to be operated, wherein a dipole antenna-form sensor measures a change in a specific parameter depending on a blood glucose level. The apparatus measures the blood glucose in a non-invasive manner,
(Continued)

wherein a display unit that is present outside the human body receives the parameter value through wireless communication and displays a corresponding blood glucose level.

8 Claims, 5 Drawing Sheets (51) Int. Cl.
| | |
|---|---|
| H02J 50/10 | (2016.01) |
| A61B 5/00 | (2006.01) |
| A61B 5/1473 | (2006.01) |
| H01Q 9/16 | (2006.01) |
| H02J 7/02 | (2016.01) |
| H01Q 9/28 | (2006.01) |

(52) U.S. Cl.
CPC ............ *A61B 5/145* (2013.01); *A61B 5/1473* (2013.01); *A61B 5/6876* (2013.01); *A61B 5/742* (2013.01); *H01Q 9/16* (2013.01); *H01Q 9/28* (2013.01); *H02J 7/02* (2013.01); *H02J 7/025* (2013.01); *H02J 50/10* (2016.02); *A61B 2560/0219* (2013.01); *A61B 2562/164* (2013.01); *A61B 2562/166* (2013.01)

(58) Field of Classification Search
CPC .................. A61B 5/6876; A61B 5/145; A61B 2560/0219; H02J 50/10
See application file for complete search history.

(56) References Cited

U.S. PATENT DOCUMENTS

| | | | | |
|---|---|---|---|---|
| 2013/0303866 | A1* | 11/2013 | Fischer | A61B 5/0507 600/316 |
| 2015/0039007 | A1* | 2/2015 | Chen | A61B 5/150435 606/183 |
| 2015/0051466 | A1* | 2/2015 | Afroz | A61B 5/053 600/377 |
| 2016/0149292 | A1* | 5/2016 | Ganton | G06K 19/0723 600/300 |
| 2019/0053741 | A1* | 2/2019 | Chaudhry | A61B 5/14546 |

FOREIGN PATENT DOCUMENTS

| | | |
|---|---|---|
| JP | 2013-055423 A | 3/2013 |
| KR | 10-2005-0119992 A | 12/2005 |
| KR | 10-2009-0084409 A | 8/2009 |
| KR | 10-1099641 B1 | 12/2011 |
| KR | 10-2013-0012990 A | 2/2013 |
| KR | 10-2013-0110190 A | 10/2013 |
| KR | 10-2016-0050399 A | 5/2016 |
| KR | 10-2016-0107086 A | 9/2016 |
| KR | 10-2016-0108531 A | 9/2016 |

OTHER PUBLICATIONS

Bakogianni et al. An Implantable Planar Dipole Antenna for Wireless MedRadio-Band Biotelemetry Devices. IEEE Antennas and Wireless Propagation Letters, vol. 15, 2016. (Year: 2016).*

Bababjanyan et al. Real-Time Noninvasive Measurement of Glucose Concentration Using a Microwave Biosensor. Hindawi Publishing Corporation Journal of Sensors. (Year: 2010).*

Afroz et al. Implantable SiC based RF antenna biosensor for continuous glucose monitoring. (Year: 2013).*

Kumar et al. Measuring Blood Glucose Levels with Microwave Sensor. International Journal of Computer Applications. vol. 72—No. 15, Jun. 2013. (Year: 2013).*

International Search Report for related International Application No. PCT/KR2017/010302; report dated Dec. 20, 2017.

* cited by examiner

IMPLANTABLE BLOOD GLUCOSE MEASURING APPARATUS AND METHOD

CROSS-REFERENCE TO RELATED APPLICATION

This Application is a 35 USC § 371 US National Stage filing of International Application No. PCT/KR2017/010302 filed on Sep. 20, 2017 and claims priority under the Paris Convention to South Korean Patent Application No. 10-2017-0012877 filed on Jan. 26, 2017.

TECHNICAL FIELD

One or more example embodiments relate to a method and apparatus for measuring blood glucose and, more particularly, to a method and apparatus for measuring blood glucose using a sensor implanted in a human body, not invasively but non-invasively, thereby preventing an occurrence of pain.

BACKGROUND ART

Diabetes is one of diseases that hundreds of millions of people worldwide have. Also, the diabetes occurs when insulin controlling blood glucose is not produced or deficient, or when insulin function is impaired. The number of diabetic patients is steadily increasing.

Although there are various medical therapies and diets to manage the diabetes, blood glucose measurement is a basis thereof. A blood glucose measuring apparatus is an indispensable diagnostic device for diabetic patients.

Various methods have been developed for self-measuring of blood glucose. However, a common method is to measure a concentration of glucose in blood by stabbing a finger. Therefore, there is a desire for a non-invasive blood glucose self-measuring apparatus.

SUMMARY OF THE DISCLOSURE

According to an aspect, there is provided a blood glucose measuring apparatus including a measurer including a dipole antenna, an integrated circuit (IC) chip, a receiving coil, and a flexible printed circuit board and implanted in a human body to measure a predetermined parameter of the dipole antenna, a charger configured to supply power to the measurer based on a wireless power transfer scheme, and a display configured to display blood glucose by converting information on the parameter information transmitted from the measurer.

The measurer may be configured to transmit the information on the parameter to the display using a frequency band of 400 megahertz (MHz) to 405 MHz.

The information on the parameter may be $S_{11}$ parameter information of the dipole antenna. The dipole antenna sensor may have a length of 10 millimeters (mm) to 50 mm.

The display may be configured to convert the $S_{11}$ parameter information into an impedance value and display a blood glucose level corresponding to the impedance value.

According to another aspect, there is also provided a method of measuring blood glucose, the method including measuring, by a measurer including a dipole antenna, an IC chip, a receiving coil, and a flexible printed circuit board and implanted in a human body, a predetermined parameter of the dipole antenna, transferring, by the measurer, information on the parameter to a display, supplying, by a charger, power to the measurer based on a wireless power transfer scheme, and displaying, by the display, blood glucose by converting the information on the parameter into blood glucose information.

The measurer may be configured to transmit the information on the parameter to the display using a frequency band of 400 MHz to 405 MHz.

The information on the parameter is $S_{11}$ parameter information of the dipole antenna sensor. The dipole antenna may have a length of 10 mm to 50 mm.

The display may be configured to convert the $S_{11}$ parameter information into an impedance value and display a blood glucose level corresponding to the impedance value.

DETAILED DESCRIPTION

Hereinafter, example embodiments will be described in detail with reference to the accompanying drawings. It should be understood, however, that there is no intent to limit this disclosure to the particular example embodiments disclosed. Like numbers refer to like elements throughout the description of the figures.

Terminologies used herein are defined to appropriately describe the example embodiments of the present disclosure and thus may be changed depending on a user, the intent of an operator, or a custom. Accordingly, the terminologies must be defined based on the following overall description of this specification.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
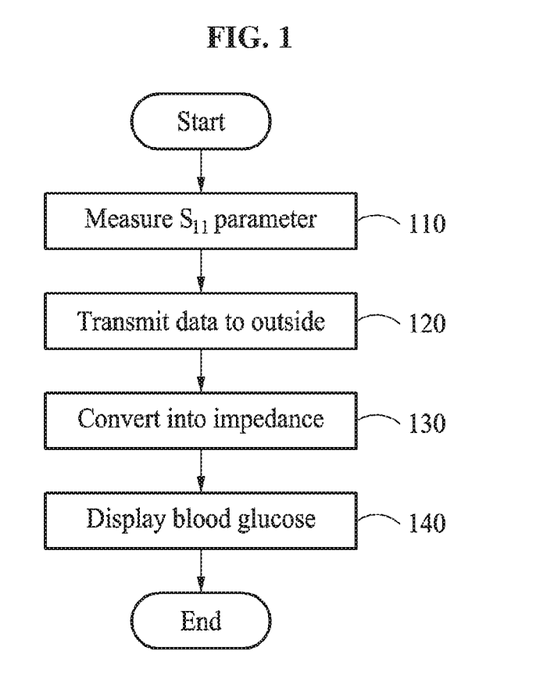
FIG. 1 is a flowchart illustrating a measurement process of a blood glucose measuring apparatus in a stepwise manner according to an example embodiment.

FIG. 1 is a flowchart illustrating a measurement process of a blood glucose measuring apparatus in a stepwise manner according to an example embodiment. Operation 110 is an operation of measuring a predetermined parameter of a dipole antenna sensor, operation 120 is an operation of transmitting measured data to an outside, and operation 130 is an operation of converting the transmitted data into an impedance value. Operation 140 is an operation of displaying blood glucose based on the impedance value.

Specifically, operation 110 may be an operation of measuring an $S_{11}$ parameter of the dipole antenna sensor. In general, when a waveform having a frequency is transmitted to an antenna, a reflection coefficient may change based on a medium around the antenna. A degree to which the waveform of the antenna changes may vary based on an amount of glucose in a blood vessel. Thus, a change in blood glucose may cause a change in permittivity of the antenna, and a sensor may accept the change as a change in reflection coefficient and perform measurement. The $S_{11}$ parameter may refer to a parameter that transmits a waveform to a predetermined port and analyzes a signal returning to the port.

In terms of a dipole antenna, when a length of an antenna is ½ of a used wavelength, polarities of potential distribution on a vertical or horizontal line may be opposite based on a center of the antenna so as to act like a dipole. Such antenna may be referred to as the dipole antenna.

The dipole antenna sensor may be inserted into a human body and located in a blood vessel. A waveform having a frequency may be transmitted to a predetermined port of the dipole antenna and an $S_{11}$ parameter returning to the port may be measured. A value of the $S_{11}$ parameter may vary based on a blood glucose level. Also, the $S_{11}$ parameter value may proportionally increase as the blood glucose level increases. Thus, by analyzing the $S_{11}$ parameter value, a blood glucose level corresponding to the $S_{11}$ parameter value may be obtained.

Operation 120 is an operation of transmitting the measured $S_{11}$ parameter value to a display outside a human body. Specifically, the $S_{11}$ parameter value may be transmitted using wireless communication technology, and the display may receive the $S_{11}$ parameter value.

In operation 130, the display converts the received value into an impedance value. Since it is difficult to directly convert the measured parameter value into the blood glucose, the measured parameter value may be converted into an impedance first. The impedance value may proportionally increase as a blood glucose value corresponding to the converted impedance value increases and, accordingly, a blood glucose level corresponding to the calculated impedance value may be displayed.

In operation 140, the display displays a blood glucose. The display may display a blood glucose value corresponding to data converted into the impedance value in operation 130. The display may not only perform a function of displaying the blood glucose level but also calculate the impedance value obtained from the $S_{11}$ parameter value and display a blood glucose level value corresponding to the impedance value. The display may display the blood glucose as a value in units of, for example, milligrams per deciliters (mg/dl) together with a risk by using red, yellow, and green warning lights based on the risk of the blood glucose level.

Figure 2:
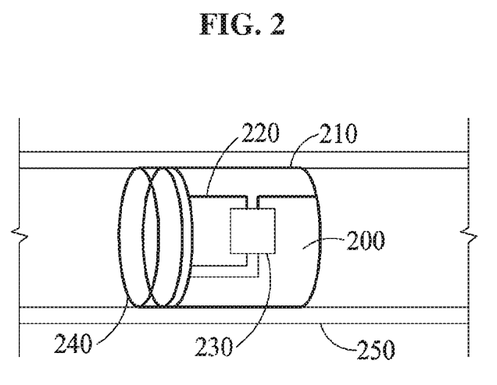
FIG. 2 illustrates a structure of a measurer insertable in a blood vessel in a human body according to an example embodiment.

FIG. 2 illustrates a structure of a measurer 200 according to an example embodiment. The measurer 200 may include a flexible printed circuit board 210, a dipole antenna, an integrated circuit (IC) chip 230, and a receiving coil 240. The measurer 200 may be disposed in a blood vessel 250 of a user.

Specifically, the flexible printed circuit board 210 may function to connect components in a circuit manner. The flexible printed circuit board 210 may be located in the blood vessel and formed in, for example, a cylindrical shape having both sides opened to maintain a smooth flow of blood. The flexible printed circuit board 210 may connect a dipole antenna 220 and the IC chip 230, and connect the IC chip 230 and the receiving coil 240.

The dipole antenna 220 may be connected to the IC chip 230 and have a horizontally long shape. The dipole antenna 220 may be used to measure an $S_{11}$ parameter. The IC chip 230 may output a waveform having a predetermined frequency to the dipole antenna, and measure a return signal. A value of the return signal may be an $S_{11}$ parameter value, and the $S_{11}$ parameter value may be transmitted to an external display according to the Medical Implant Communication Service (MICS) which is a medical instrument standard. Because a high data transmission rate is not required due to device characteristics, an implementation may be performed by focusing on physical safety and power consumption instead of a data transmission rate. The IC chip 230 may be implemented in a size of 1 millimeter (mm)×1 mm or less according to an embodiment.

The receiving coil 240 may be used to supply power to the blood glucose measuring apparatus. Due to the characteristic of the apparatus inserted in the blood vessel, it is advantageous to supply power wirelessly only when blood glucose measurement is performed rather than embedding a battery for continuous operation. In general, three wireless power transfer schemes, for example, an inductive coupling scheme, a magnetic resonance scheme, and an electromagnetic scheme may be used. Among the schemes, the magnetic resonance scheme may be employed. The magnetic resonance scheme may be suitable for transmitting electric power through a human body since a reaching distance is several centimeters to several meters and an influence of a surrounding environment is relatively small.

In the magnetic resonance scheme, four coils, for example, a power coil, a first coil, a second coil, and a load coil may be used. The receiving coil 240 may include the second coil and the load coil. The power coil may be a coil included in the charger to supply power. The receiving coil 240 may be included in the measurer 200 inserted into the human body and receive the power. The first coil and the second coil may be coils used for increasing a transmitting and receiving efficiency. The first coil and the second coil may be formed with a high-conductivity material to increase wireless power transfer efficiency due to a high-frequency current. Thus, the power may be supplied to the power coil by a power source and transferred to the first coil based on a magnetic induction scheme. The first coil may store the power through resonance and transfer the power to the second coil. In a case of power transmission performed between the first coil and the second coil based on a magnetic resonance phenomenon, the wireless power transfer efficiency may increase two resonance coils are the same. The second coil may transfer the power to the load coil based on the magnetic induction scheme.

Figure 3:
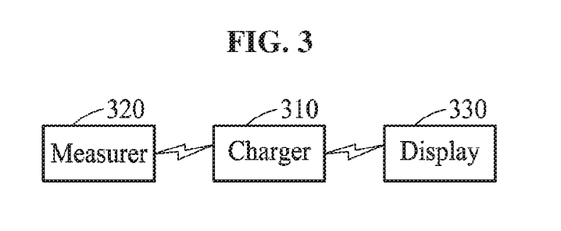
FIG. 3 illustrates a connection relationship of a blood glucose measuring apparatus according to an example embodiment.

FIG. 3 illustrates a configuration of a blood glucose measuring apparatus according to an example embodiment. A blood glucose measuring apparatus may include a measurer 310 to measure a parameter for blood glucose calculation, a charger 320 to supply power to the measurer, and a display 330 to perform data conversion and display of blood glucose. The measurer 310 may wirelessly receive power from the charger 320 and transmit a measured S parameter value to the display 330.

The charger 320 may supply power to the measurer 310 using a wireless power transfer scheme. When measuring blood glucose, a user may bring the measurer 310 close to the charger 320 so that the power is wirelessly supplied to the measurer 310. The wireless power transfer scheme will be described in detail as follows. The charger 320 may include a power coil and a first coil. The power coil may generate power to be supplied and transmit the power to the second coil. The second coil may transmit the power to a load coil. A scheme for transmitting the power may be based on a magnetic resonance. For example, a frequency band used here may be, but is not limited to, 13.56 megahertz (MHz) (ISM Band), which is not harmful and does not affect the human body. The coils used for wireless power transfer may have a low specific absorption rate (SAR) of electromagnetic waves, which is a measure of harmfulness to the human body. Also, the receiving coil may be located at an edge of the measurer to increase a power reception rate.

As such, the charger 320 may transmit the power to the measurer 310, and the measurer may operate only while receiving the power. Thus, when the measurer 310 is not brought close to the charger 320, the measurer 310 may not operate and be off. The measurer 310 may operate when the user brings the measurer 310 close to the charger 320 at a desired time for measurement.

The display 330 may receive $S_{11}$ parameter information transmitted from the measurer 310 and convert the parameter value into an impedance value. The display 330 may obtain a blood glucose value corresponding to the converted impedance value and display the blood glucose value to be confirmed by the user. The display 330 may display a blood glucose level as a specific value in units of, for example, mg/dl.

Also, red, yellow, and green warning lights may be included. Each of the warning lights may be turned on when the measured blood glucose level value is present in a preset range. For example, the red warning light may be turned on when the blood glucose level is greater than 150 mg/dl, the yellow warning light may be turned on when the blood glucose level is greater than 100 mg/dl and less than or equal to 150 mg/dl, and the green warning light may be turned on when the blood glucose level is less than or equal to 100 mg/dl.

Figure 4:
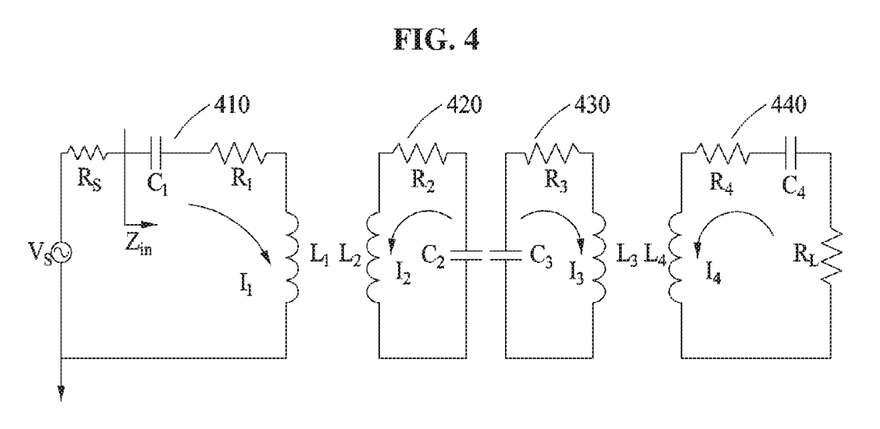
FIG. 4 illustrates a configuration of a magnetic resonance-based wireless power transfer system according to an example embodiment.

FIG. 4 illustrates a structure of a coil used for wireless power transfer according to an example embodiment. A reference numeral 410 refers to a power coil, a reference numeral 420 refers to a first coil, a reference numeral 430 refers to a second coil, and a reference numeral 440 refers to a load coil. Because a transmission efficiency is relatively low when power transmission is performed using the power coil 410 and the load coil 440 based on a magnetic resonance scheme, the first coil 420 and the second coil 430 may be used.

The power coil 410 may transmit power generated from a power source $V_S$ to a first transmission coil. Here, a power transmission scheme may be an inductive coupling scheme. The first coil 420 having received the power through the wireless power transfer may transfer the power to the second coil 430 through the wireless power transfer. Since the first coil 420 and the second coil 430 are the same coil, and the power transmission scheme is the inductive coupling scheme, an efficiency may increase during the power transmission. The second coil 430 having received the power may transmit the power to the load coil 430, and the power transmission scheme used here may be the inductive coupling scheme. Finally, the load coil 440 may operate a measurer using the received power.

Figure 5:
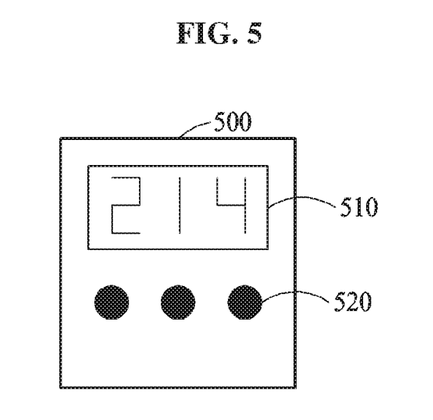
FIG. 5 illustrates a configuration of a display according to an example embodiment.

FIG. 5 illustrates a configuration of a display according to an example embodiment. A display 500 may include a portion 510 in which a blood glucose level is displayed and a warning light 520.

The portion 510 in which a blood glucose level is displayed may represent a blood glucose level measured by a measurer by digits in units of mg/dl. In FIG. 5, for example, a value "214" is indicated in the portion 510.

The warning light 520 may include, for example, three parts of red, yellow, and green, but is not limited thereto and may be refined or simplified. For example, when a diabetic patient has a blood glucose level of 214 mg/dl, the red light may be turned on to alert the patient intuitively to be in a danger condition.

An $S_{11}$ parameter value of a dipole antenna may be measured while varying a blood glucose level. As the blood glucose level increases, the $S_{11}$ parameter value may also increases. The S parameter value may change proportionally to a blood glucose concentration, and a change in $S_{11}$ parameter may be converted into an impedance value proportional thereto. As such, there is a proportional relationship in which the impedance value increases as a value of the blood glucose level increases. The display of the blood glucose measuring apparatus may display a blood glucose level based on an impedance value calculated using a value of previously input data. A method of displaying the blood glucose level may be as described with reference to FIG. 5.

The units described herein may be implemented using hardware components and software components. For example, the hardware components may include microphones, amplifiers, band-pass filters, audio to digital converters, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The methods according to the above-described embodiments may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well-known and available to those having skill in the computer software arts. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations and methods described above, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. A blood glucose measuring apparatus comprising:
a measurer comprising a dipole antenna, an integrated circuit (IC) chip configured to transmit a waveform of a predetermined frequency to the dipole antenna, a receiving coil, and a flexible printed circuit board, the measurer configured to be implanted in a blood vessel of a human body, to measure a predetermined parameter of the dipole antenna, and to transmit information on the parameter, the parameter being a reflection coefficient of the dipole antenna based on a waveform transmitted in the blood vessel from the IC chip to the dipole antenna;
a charger configured to supply power to the measurer based on a wireless power transfer scheme; and
a display configured to receive information on the parameter from the measurer, convert the information into a blood glucose level, and display the blood glucose level.

2. The blood glucose measuring apparatus of claim 1, wherein the measurer is configured to transmit the information on the parameter to the display using a frequency band of 400 megahertz (MHz) to 405 MHz.

3. The blood glucose measuring apparatus of claim 1, wherein the dipole antenna has a length of 10 millimeters (mm) to 50 mm.

4. The blood glucose measuring apparatus of claim 3, wherein the display is configured to convert the parameter information into an impedance value and the displayed blood glucose level corresponds to the impedance value.

5. A method of measuring blood glucose, the method comprising:
providing a measurer, the measurer configured to be implanted in a blood vessel of a human body and comprising a dipole antenna, an integrated circuit (IC) chip, a receiving coil, and a flexible printed circuit board;
implanting the measurer into a blood vessel of a human body;
transmitting to the dipole antenna, by the IC chip, a waveform of a predetermined frequency through the blood vessel;
measuring, by the measurer, a predetermined parameter of the dipole antenna, the parameter being a reflection coefficient of the dipole antenna based on the waveform transmitted in the blood vessel;
transferring, by the measurer, information on the parameter to a display;
supplying, by a charger, power to the measurer based on a wireless power transfer scheme; and
displaying, by the display, a blood glucose level by converting the information on the parameter into the blood glucose level.

6. The method of claim 5, wherein the measurer is configured to transmit the information on the parameter to the display using a frequency band of 400 megahertz (MHz) to 405 MHz.

7. The method of claim 5, wherein the dipole antenna has a length of 10 millimeters (mm) to 50 mm.

8. The method of claim 7, wherein the display is configured to convert the parameter information into an impedance value and the displayed blood glucose level corresponds to the impedance value.

* * * * *